(12) United States Patent
Matsuzawa et al.

(10) Patent No.: US 6,420,305 B1
(45) Date of Patent: Jul. 16, 2002

(54) SOLID ACID CATALYST, METHOD FOR PRODUCING THE SAME AND REACTION METHOD USING THE SAME

(75) Inventors: Kenji Matsuzawa; Kohjiroh Aimoto; Kazuhiro Seki, all of Toda (JP)

(73) Assignee: Japan Energy Corporation, Tokyo (JP)

(*) Notice: Subject to any disclaimer, the term of this patent is extended or adjusted under 35 U.S.C. 154(b) by 0 days.

(21) Appl. No.: 09/622,345

(22) PCT Filed: Feb. 26, 1999

(86) PCT No.: PCT/JP99/00922

§ 371 (c)(1),
(2), (4) Date: Aug. 11, 2000

(87) PCT Pub. No.: WO99/44738

PCT Pub. Date: Sep. 10, 1999

(30) Foreign Application Priority Data

Mar. 4, 1998 (JP) ............................................... 10-67614

(51) Int. Cl.$^7$ ........................ B01J 27/043; B01J 23/00; C07C 2/02; C07C 6/12; C07C 2/64

(52) U.S. Cl. ...................... 502/222; 502/349; 502/351; 502/355; 585/375; 585/422; 585/446; 585/458; 585/442; 585/444; 585/468; 585/470; 585/480; 585/482; 585/515; 585/526; 585/661; 585/668; 585/730; 585/750; 585/751

(58) Field of Search ................................. 585/375, 422, 585/446, 458, 442, 444, 468, 470, 480, 482, 515, 526, 661, 668, 730, 750, 751; 502/222, 349, 351, 355

(56) References Cited

U.S. PATENT DOCUMENTS

| | | | |
|---|---|---|---|
| 3,032,599 A | 5/1962 | Holm et al. | |
| 4,835,129 A | 5/1989 | Travers et al. | 502/37 |
| 5,036,035 A | 7/1991 | Baba et al. | 502/221 |

FOREIGN PATENT DOCUMENTS

| | | |
|---|---|---|
| EP | 0 925 830 | 6/1999 |
| JP | 59-6181 | 2/1984 |
| JP | 61-254250 | 11/1986 |
| JP | 2-71840 | 3/1990 |
| JP | 5-29503 | 4/1993 |
| JP | 5-29504 | 4/1993 |
| JP | 5-29505 | 4/1993 |
| JP | 5-29506 | 4/1993 |
| JP | 5-96171 | 4/1993 |
| JP | 9-38494 | 2/1997 |
| WO | WO 93/00164 | 1/1993 |

OTHER PUBLICATIONS

Synthesis of solid superacids by metal oxides and their catalytic action, by Kazushi Arata, Trends in Physical Chemistry, vol. 2, 1991, pp. 1–24.

*Primary Examiner*—Thuan D. Dang
(74) *Attorney, Agent, or Firm*—Flynn, Thiel, Boutell & Tanis, P.C.

(57) ABSTRACT

A method for producting a solid acid catalyst is provided which produces a shaped material of a solid acid catalyst containing a sulfureous component but have a high activity and having a practically sufficient handleability and mechanical strength involves the steps of (a) fabricating a support containing a portion of zirconia and/or hydrated zirconia and a portion of alumina and/or hydrated alumina and having a peak diameter in the range of 0.05 to 1 μm in a pore diameter distribution of 0.05 to 10 μm; and having a sulfureous component supported on the support or (b) fabricating a support containing a portion of zirconia and/or hydrated zirconia and a portion of alumina and/or hydrated alumina and including pores having a pore diameter of not less than 0.05 μm and not more than 1 μm occupying a pore volume of 0.05 to 0.5 ml/g and pores having a pore diameter of about 1 μm and not more than 10 μm occupying a pore volume of below 0.05 ml/g; and having a sulfureous component supported on the support.

15 Claims, No Drawings

SOLID ACID CATALYST, METHOD FOR PRODUCING THE SAME AND REACTION METHOD USING THE SAME

TECHNICAL FIELD

The present invention relates to a solid acid catalyst having a high activity in an acid-catalyzed reaction system and having easy handleability and a method for producing the same.

BACKGROUND ART

In the chemical industry, there have been known acid-catalyzed reactions such as alkylation reactions, esterification reactions, and isomerization reactions. Hitherto, in these reactions, there have been used acid catalysts such as sulfuric acid, aluminum chloride, hydrogen fluoride, phosphoric acid, and paratoluenesulfonic acid. However, these acid catalysts have metal corroding properties so that the use of costly anticorrosive materials for a production apparatus or anti-corrosive treatment of a production apparatus has been required. Usually, not only is it difficult to separate the catalysts from the reactants after the reaction but also it is necessary to conduct disposal of waste acid and it is also inevitable to undergo a complex process such as alkali washing. Also, there are many problems from the environment viewpoints. Further, it has been very difficult to reuse the catalysts.

In order to solve these problems, there has been proposed a solid acid catalyst containing a sulfate group which has been obtained by contacting a hydroxide or hydrated hydroxide of a metal belonging to group IV of the Periodic Table with a solution containing a sulfureous component and calcining the mixture at 350 to 800° C. (Japanese Patent Publication No. 59-6181). The solid acid catalyst has an acidity higher than that of 100% sulfuric acid (Hammett acidity function $H_0$ is −11.93). Because of their high acidity, the solid acid catalysts exhibit high catalyzing power in various acid-catalyzed reactions and have advantageous features that they show low corrosiveness, can be separated easily from the reactants, do not require disposal of waste acids, and can be reused, so they are expected to be substituted for conventional acid catalysts.

It has been also known that a catalyst obtained by impregnating platinum into a catalyst that has been obtained by the calcination of a sulfureous component-containing zirconia gel exhibits good activity for an isomerization reaction of hydrocarbons (U.S. Pat. No. 3,032,599).

As the methods for producing metal oxide catalysts that contain a platinum-family metal and a sulfureous component and are used mainly in the isomerization of hydrocarbons, there have been disclosed a method in which the step of calcination has been eliminated between the steps of treatment with a sulfureous compound and supporting of a platinum-family metal, a method in which the order of the steps of treatment with a sulfureous compound and supporting of a platinum-family metal are reversed, and a method in which the kind of sulfureous compound is changed in Japanese Patent Publication Nos. 5-29503, 5-29504, 5-29505, and 5-29506.

Also, it has been known that a solid acid catalyst obtained by adding a sulfureous compound to aluminum hydroxide or oxide followed by calcination exhibits an acidity higher than 100% sulfuric acid (Japanese Patent Application Laid-open No. 5-96171, Arata, Trends in Physical Chemistry, vol. 2, item 1 (1991)).

Japanese Patent Application Laid-open No. 9-38494 discloses a method for the production of a metal oxide shaped catalyst treated with a sulfate group. The method is characterized by preliminarily calcining a shaped material shaped from a metal hydroxide and boehmite at a temperature of 300° C. to 500° C. and then treating it with a sulfate group, which is a method for shaping a catalyst utilizing alumina as a binder. However, its catalytic activity is decreased as compared with a powder catalyst containing no boehmite due to the shaping with the addition of the boehmite. Also, it is disclosed that a shaped material obtained by using a metal hydroxide and boehmite powder, when dried at a temperature below 300° C., will be pulverized and destroyed by addition of water and that a catalyst obtained by kneading a mixture of platinum-containing sulfated zirconia catalyst powder (a powdery catalyst composed of zirconia supporting thereon platinum and a sulfate group) and boehmite powder with the addition of water, followed by shaping and calcination has a greatly decreased catalytic activity.

Solid catalysts, when utilized, must be shaped catalysts, which are easy to separate from the reactants and reuse as opposed to the powder form. However, even if catalysts have sufficient catalytic activity when they are in the form of a powder, shaping of them will make it impossible to obtain the mechanical strength that is required at the time of reaction/production or their catalytic activity will decrease accompanying their shaping. Thus, there has been made no report on a method for producing a solid acid shaped catalyst that satisfies the characteristics required as a catalyst and has a required mechanical strength.

DISCLOSURE OF THE INVENTION

The present invention solves these problems and provides a solid acid catalyst having a sufficiently high activity, an easy handleability sufficient for practical use and a sufficient mechanical strength, and which is a shaped product of the solid acid catalyst containing a sulfureous component, a method for producing the same, and a reaction method using such a catalyst.

As a result of extensive research on a method for producing the solid acid catalyst, the present inventors have now found that kneading zirconium hydroxide having specific physical properties, pseudoboehmite having specific physical properties, and ammonium sulfate, followed by shaping and calcination can give rise to a solid acid catalyst having an excellent catalytic activity and a sufficient mechanical strength, and further made research on the catalyst to complete the present invention.

According to a first aspect of the present invention, a method for producing a solid acid catalyst comprises the steps of: fabricating a support comprising a portion of zirconia and/or hydrated zirconia and a portion of alumina and/or hydrated alumina and having a peak diameter in the range of 0.05 to 1 $\mu$m in a pore diameter distribution of 0.05 to 10 $\mu$m; and having a sulfureous component supported on the support.

According to a second aspect of the present invention, a method for producing a solid acid catalyst comprises the steps of: fabricating a support comprising a portion of zirconia and/or hydrated zirconia and a portion of alumina and/or hydrated alumina in which pores having a pore diameter of not less than 0.05 $\mu$m and not more than 1 $\mu$m occupy a pore volume of 0.05 to 0.5 ml/g and pores having a pore diameter of above 1 $\mu$m and not more than 10 $\mu$m occupy a pore volume of below 0.05 ml/g; and having a sulfureous component supported on the support.

According to a third aspect of the present invention, a method for producing a solid acid catalyst comprises the steps of: kneading powder comprising zirconium hydroxide and/or hydrated oxide whose agglomerated particles have an average particle diameter of 0.2 to 10 μm with powder comprising aluminum hydroxide and/or hydrated oxide having a fibrous particle form, shaping the mixture to fabricate a support; and having a sulfureous component supported on the support. In this case, it is preferred that the above-mentioned support has a peak diameter in the range of 0.05 to 1 μm in a pore diameter distribution of 0.05 to 10 μm and in which pores having a pore diameter of not less than 0.05 μm and not more than 1 μm occupy a pore volume of 0.05 to 0.5 ml/g and pores having a pore diameter of above 1 μm and not more than 10 μm occupy a pore volume of below 0.05 ml/g. It should be noted that it is preferred to conduct the step of fabricating a support and the step of having a sulfureous component supported on the support in one step simultaneously.

The solid acid catalyst of the present invention is a catalyst which is constituted by a portion of zirconia and/or hydrated zirconia and a portion of alumina and/or hydrated alumina, contains a sulfureous component, and is used in acid-catalyzed reactions, the catalyst having a pore diameter distribution of 0.05 to 10 μm with a peak pore diameter being in the range of 0.05 to 1 μm. Alternatively, it is a catalyst which is constituted by a portion of zirconia and/or hydrated zirconia and a portion of alumina and/or hydrated alumina, contains a sulfureous component and is used in acid-catalyzed reactions, in which catalyst pores having a pore diameter of not less than 0.05 μm and not more than 1 μm occupy a pore volume of 0.05 to 0.5 ml/g and pores having a pore diameter of above 1 μm and not more than 10 μm occupy a pore volume of below 0.05 ml/g. For the acid-catalyzed reactions, the above-mentioned solid acid catalyst is used preferably for the conversion reaction of hydrocarbons.

BEST MODE FOR CARRYING OUT THE INVENTION

Zirconia Powder

The powder comprising zirconium hydroxide and/or hydrated oxide for use in the production of solid acid catalysts (hereinafter, simply referred to as "zirconia powder") has an increased crushing strength, and zirconia tends to be stabilized when the zirconia powder is converted into an amorphous form, which has no definite crystal structure as examined by X-ray or electron beam diffraction analysis. Use of agglomerated particles having an average particle diameter of 0.2 to 10 μm, particularly 0.2 to 5 μm, and more particularly 0.5 to 2 μm is preferred for increasing the activity and mechanical strength of the catalyst. The average particle diameter of agglomerated particles can be measured, for example, by a method which involves irradiating a laser beam onto a group of particles dispersed in water and calculating from the scattered light.

The zirconia powder may be produced by any method but generally it can be obtained by the neutralization or hydrolysis of zirconium salts or organic metal compounds, for example, oxychlorides, alcoholates, chlorides, sulfates, nitrates, and oxysulfates. The main component of zirconia powder is a mixture of zirconium hydroxide and hydrated zirconium oxide, zirconium hydroxide, or hydrated zirconium oxide.

Further, the zirconia powder can be used as a complex metal hydroxide and/or hydrated complex metal oxide. To the hydroxide and/or hydrated oxide of zirconium may be added hydroxides and/or hydrated oxides of other metals. As the other metals there can be advantageously used titanium, hafnium, vanadium, chromium, manganese, iron, silicon, tin, gallium, etc. Compounds of such other metals may be complex metal compounds. However, as the zirconia powder, there are used preferably those which consist substantially of only zirconium as the metal component, more specifically, those which contain zirconia as a metal in an amount of at least 70% by weight, particularly at least 90% by weight, based on the total weight of metals in the zirconia powder.

Alumina Powder

The powder which comprises aluminum hydroxide and/or hydrated oxide for use in the production of the solid acid catalyst (hereinafter, simply referred to as "alumina powder") preferably has a fibrous particle form in order to increase the mechanical strength of the shaped catalyst, particularly the water stability of the shaped pellets. More specifically, the shape of the fibrous particle form is preferably such that its aspect ratio is greater than 10, particularly greater than 20. Usually, the upper limit of the aspect ratio is about 200. Here, the aspect ratio means a ratio of the lengths of the minor axis and the major axis of a particle ([length of major axis]/[length of minor axis]) and can be obtained, for example, by observing the alumina powder on a transmission electron microscope or the like, measuring the ratios of the lengths of the minor axis and the major axis, and calculating their average values. When the particles are spherical, the aspect ratio is 1, which is the least value. Typically, such a particle form can be obtained as a primary particle of 0.1 μm or more in the major axis and a secondary particle whose primary particles are oriented in a certain direction. Also, particles of other forms than fibrous form, for example, plate-like particles, may be contained so far as the aspect ratio that is an average value falls within the range of greater than 10, particularly greater than 20.

The alumina powder is preferably of such a form that its agglomerated particles have an average particle diameter of 0.5 to 50 μm, particularly 1 to 40 μm, and more particularly 1 to 20 μm. Usually, the agglomerated particle is an agglomerate of fibrous particles. As the alumina powder, there can be used those manufactured by various production methods. Particularly, it is preferred to use aluminum hydrated oxide having a boehmite structure, such as pseudoboehmite, because there can be obtained an increased catalytic activity. Use of α-alumina or γ-alumina as the alumina powder will result in a decrease in mechanical strength relatively and a decrease in catalytic activity.

Support

The support which can preferably be used in the present invention has a peak diameter in the range of 0.05 to 1 μm in a pore diameter distribution of 0.05 to 10 μm, and particularly its pores having a pore diameter of not less than 0.05 μm and not more than 1 μm occupy a pore volume of 0.05 to 0.5 ml/g and pores having a pore diameter of above 1 μm and not less than 10 μm occupy a pore volume of below 0.05 ml/g. It is preferred for increasing the mechanical strength of the catalyst that it has a peak diameter in the range of 0.05 to 1 μm, particularly 0.05 to 0.5 μm, but no other peak in a pore diameter distribution of 0.05 to 10 μm and that pores having a pore diameter of not less than 0.05 μm and not more than 1 μm occupy a pore volume of 0.05 to 0.5 ml/g, particularly 0.05 to 0.3 ml/g, and pores having a pore diameter of above 1 μm and not more than 10 μm occupy a pore volume of below 0.05 ml/g, particularly below 0.02 ml/g.

The pore distribution can be measured by a mercury injection method in which it is assumed that the contact angle of mercury is 140° and surface tension is 480 dynes/ cm and all the pores are cylindrical. The pore size distribution having a peak means that a so-called pore distribution curve obtained by plotting a differential value of cumulative pore volume by pore diameter versus pore diameter has a clear optimal value.

The support is not a powder but of a shaped form and it is easy to obtain a support of 0.5 to 20 mm in size. Usually, particles having a size (length of cross-section) of 0.2 to 50 mm, particularly 0.5 to 20 mm, are used preferably. The alumina portion and zirconia portion are present in the support as particles of 0.01 to 100 μm. Such a support can be fabricated by kneading the above-mentioned zirconia powder and alumina powder with each other and shaping the mixture. However, those supports fabricated by other methods may be used so far as they have the predetermined pore structure.

For the kneading, there may be used a kneader used generally in the preparation of catalysts. Usually, a method in which raw materials are charged in the kneader, water is added thereto, and mixed with stirring vanes can be used advantageously. However, no particular limitation is posed on the order of addition of raw materials and water. When kneading, usually water is added. However, it is not always necessary to add water when the raw material powders are in the form of slurry. The liquid to be added may be an organic solvent such as ethanol, isopropanol, acetone, methyl ethyl ketone, and methyl isobutyl ketone. The temperature and period of time of kneading may vary depending on the zirconia powder and alumina powder used as raw materials. However, there is no particular limitation on such conditions so far as the conditions can give rise to a preferable pore structure. Similarly, within the range in which the properties of the catalyst of the present invention are maintained, the kneading may be performed with the addition of an acid such as nitric acid, a base such as ammonia, an organic compound, a binder, a ceramic fiber, a surfactant, zeolite or the like.

The shaping after the kneading may be performed using a shaping method generally used in the preparation of a catalyst. Particularly, since shaping into any desired form, such as pellet form and honeycomb form, can be efficiently performed, extrusion molding using a screw type extruder can be employed preferably. The size of the shaped material is not limited particularly. However, usually, it is shaped so as to have a cross-section of 0.5 to 20 mm in length. For example, in the case of cylindrical pellets, there can be easily obtained those that usually have a diameter of about 0.5 to about 10 mm, and a length of about 0.5 to about 15 mm.

The calcination after the shaping is carried out in a gas atmosphere such as air or nitrogen. It is preferred that the calcination is performed also for the purpose of having a sulfureous component supported on the support since this makes the process simple.

Supporting of Sulfureous component

The sulfureous component can be supported by a support by contacting a sulfureous compound with the support followed by heat treatment. As the sulfureous compound, there can be cited, for example, sulfuric acid, ammonium sulfate, sulfurous acid, ammonium sulfite, and thionyl chloride. Ammonium sulfate and ammonium sulfite are preferred since they are less corrosive to the production apparatus. The sulfureous compound may be used as it is or as a solution such as an aqueous solution. The sulfureous compound may be solid or liquid and there is no particular limitation on the concentration of solutions so that it can be formulated taking into consideration the amount of solution necessary for kneading or the like. The amount of sulfureous compound to be added is preferably such that the amount of sulfur in the finally obtained solid acid catalyst occupies 0.2 to 10% by weight, particularly 1 to 10% by weight.

It is preferred to have the sulfureous compound supported on a support simultaneously with the fabrication of the support. The catalyst of the invention can be fabricated by kneading the zirconia powder, alumina powder, and sulfureous compound, shaping and calcining the resultant mixture. The kneading and shaping can be performed in the same manner as in the case of fabricating the support. It is preferred in view of catalytic activity that the weight of the sulfureous compound is 3 to 40% by weight, particularly 10 to 30% by weight, based on its total weight before calcination. The calcination is preferably carried out at a temperature at which a tetragonal crystal structure of zirconium oxide is obtained. This structure can be confirmed by X-ray diffraction using a CuK$_\alpha$ ray, more particularly when an X-ray diffraction peak ratio of 2θ=28.2° and 2θ=30.2° (hereinafter, abbreviated as "S28.2/S30.2 ratio"; here, S28.2 designates the area of a peak of a tetragonal crystal of zirconia at 2θ=28.2° while S30.2 designates the area of a peak of a tetragonal crystal of zirconia at 2θ=30.2°) is 1.0 or less, preferably 0.05 or less. The presence of substantially no monoclinic crystal structure results in a higher catalytic activity.

When pseudoboehmite type alumina is used as the alumina powder, a preferred temperature is 450 to 800° C., particularly 500 to 800° C., and more particularly 600 to 800° C. and a preferred period of time of calcination is 0.1 to 20 hours. Too high a calcination temperature is undesirable since the proportion of monoclinic crystal in the crystal structure of zirconium oxide increases and the S28.2/S30.2 ratio may exceed 1 and results in a decrease in catalytic activity. Also, too low a calcination temperature is undesirable since zirconium oxide will not crystallize, with the result that catalytic activity will decrease.

In the case where a support is fabricated and then a sulfureous component is supported by the support, the sulfureous compound may be used in any form, for example, gas or an aqueous solution, so far as it can be brought into sufficient contact with the support. However, it is preferred that it is in the form of a liquid because of easier handleability. There is no particular limitation on the contacting method. However, an impregnation method by spraying, dipping, etc. and a method in which it is rendered gaseous and passed through a catalyst layer are used advantageously. After it is brought into contact with the sulfureous compound, the support is calcined at a temperature of higher than 300° C. but lower than 800° C., preferably higher than 400° C. but lower than 800° C. to obtain the target solid acid catalyst. The calcination time is usually 0.5 to 10 hours.

Used Catalyst

In the present invention, as the support there can be employed a used solid acid catalyst having a decreased activity. The solid acid catalyst before use comprises a support that is constituted by a zirconia portion having a tetragonal crystal structure and an alumina portion and a sulfureous component supported by the support. It is preferred that the support constituted by a zirconia portion having a tetragonal crystal structure and an alumina portion remains, even after use. Depending on the conditions under which it is used, there is the case where the support contains no sulfureous component.

The solid acid catalyst is preferably produced by kneading zirconia powder, alumina powder and a sulfureous compound, shaping and calcining. In this case, the kneading and shaping can be performed in the same manner as the fabrication of the support described above. In this case, it is preferred in view of catalytic activity that the weight of the sulfureous compound is 3 to 40% by weight, particularly 10 to 30% by weight, based on the total weight before the calcination. The calcination is performed at a temperature at which zirconium oxide having a tetragonal crystal structure can be obtained.

Solid Acid Catalyst

The solid acid catalyst of the present invention is a catalyst which comprises a support constituted by a portion of zirconia and/or hydrated zirconia (hereinafter, also referred to as "zirconia portion") and a portion of alumina and/or hydrated alumina (hereinafter referred to as "alumina portion") and a sulfureous component supported by the support, and which has a peak in diameter in the range of 0.05 to 1 μm in a pore diameter distribution of 0.05 to 10 μm, particularly pores having a pore diameter of not less than 0.05 μm and not more than 1 μm occupy a pore volume of 0.05 to 0.5 ml/g and pores having a pore diameter of above 1 μm and not more than 10 μm occupy a pore volume of below 0.05 ml/g. The pore structure of the catalyst can be measured in the same manner as the support and the pore structure with a pore diameter of 0.05 μm or more is substantially the same before the supporting of the sulfureous component. In particular, it is preferred for increasing the mechanical strength of the catalyst that it has a peak diameter in the range of 0.05 to 1 μm, particularly 0.05 to 0.5 μm, but no other peak in a pore diameter distribution of 0.05 to 10 μm, and that pores having a pore diameter of not less than 0.05 μm and not more than 1 μm occupy a pore volume of 0.05 to 0.5 ml/g and pores having a pore diameter of above 1 μm and not more than 10 μm occupy a pore volume of below 0.05 ml/g, particularly less than 0.02 ml/g.

The distribution of pores with a pore diameter of not more than 0.05 μm can be measured by a nitrogen adsorption method or the like. In this range, it is preferred that the pores have an average pore diameter in accordance with the size of a target reaction compound and usually 20 to 200 Å, particularly 30 to 120 Å. The crystal structure of the zirconia portion in the catalyst has an S28.2/S30.2 ratio of not more than 1.0, particularly not more than 0.05. The presence of substantially no monoclinic crystal structure will provide a higher catalytic activity. The solid acid catalyst of the present invention can exhibit an acidity higher than that of 100% sulfuric acid (Hammett acidity function $H_0$ is −11.93).

It is more preferred that the weight of the alumina portion in the total weight of the alumina portion and the zirconia portion in the catalyst is 5 to 90% by weight, preferably 5 to 50% by weight, and more particularly 10 to 40% by weight. Below this range the mechanical strength of the catalyst is decreased and zirconia is difficult to stabilize. Above this range the catalytic activity is lowered relatively. The total weight of the zirconia portion and the alumina portion in the catalyst is preferably not less than 70% by weight, particularly not less than 80% by weight from viewpoints such as catalytic activity and the strength of a shaped material.

The solid acid catalyst of the present invention, if desired, may preferably contain metal components selected from groups 8, 9, or 10 when it is used in conversion reactions such as isomerization. As the metal components to be used for the catalyst of the present invention, selected from groups 8, 9, or 10, there can appropriately be used platinum, palladium, ruthenium, nickel, etc. It is preferred to use them in the form of compounds compared to use of the metal itself. The metal compounds may be used either as anhydrides or as hydrates. Further, the metal compounds may be used singly or mixtures of two or more of them. As for the amount of the metal compounds to be added, it is preferred that they are added such that the total amount of elements of group 8, 9, or 10 in the solid acid catalyst is 0.05 to 10% by weight, particularly 0.1 to 5% by weight.

There is no particular limitation on the method of supporting the metal components. However, an impregnation method such as spraying or dipping, an ion exchange method, etc. can be used advantageously. The above-mentioned supported catalyst is calcined in a gaseous atmosphere such as air or nitrogen at a temperature of 300 to 700° C. for 0.1 to 20 hours in order to increase the activity of the catalyst.

The catalyst of the present invention is not powder but in a shaped form so that a catalyst of 0.5 to 20 mm in size can be obtained with ease. Usually, the catalyst having an average particle diameter of 0.2 to 50 mm, particularly 0.5 to 20 mm, is used.

The mechanical strength of the catalyst, obtained as the strength of a side surface crushing strength of a cylindrical pellet of 1.5 mm in diameter, is not less than 2 kg, preferably not less than 3 kg, more preferably 4 to 20 kg. The shaped solid acid catalyst of the present invention maintains its form after it is left in water. Pellets that do not maintain their form in water powder or crack during the step of supporting in the production of a catalyst or during catalytic reactions, which will lead to a decrease in yield or troubles in the process so that such pellets are undesirable in practice.

Acid-Catalyzed Reaction

The acid-catalyzed reaction to which the solid acid catalyst of the present invention is applicable includes those conventional acid-catalyzed reactions in which Lewis acid catalysts, typically aluminum chloride base catalysts or Broensted acid catalysts, typically sulfuric acid, are used. Examples of such reactions include various reactions such as isomerization, disproportionation, nitration, decomposition, alkylation, esterification, acylation, etherification, and polymerization. More specifically, the catalyst of the present invention can be used in an esterification reaction of methacrylic acid, etc., decomposition reaction of cumene hydroperoxide, alkylation reaction of phenol, ring-opening polymerization reaction of tetrahydrofuran, decomposition reaction of flons, oxidative coupling reaction of methane, etc. In particular, it can preferably be used in conversion reactions such as isomerization, decomposition, acylation, etherification, and esterification. Main reaction targets include hydrocarbons, i.e., hydrocarbons and hydrocarbon derivatives such as those derived by attaching substituent groups to the hydrocarbons, particularly hydrocarbons or oxygen-containing hydrocarbon compounds. More particularly, the catalyst of the present invention is preferably used in conversion reactions of hydrocarbons. Examples of the conversion reactions include isomerization, decomposition, acylation, etherification, and alkylation, etc.

The target of isomerization is preferably hydrocarbons in a petroleum fraction having a boiling point in the range of about −20° C. to 150° C. In particular, the catalyst of the present invention is preferably used in a reaction in which a straight chain paraffin is isomerized into a branched paraffin, or an olefin or an aromatic compound is hydrogenated to form a noncyclic or cyclic paraffin, and then further isomerized. As for the conditions for the isomerization of hydrocarbon compounds, a preferred temperature is in the range of 100 to 300° C., particularly 120 to 240° C., a preferred pressure is in the range of 1 to 50 kgf/cm², a preferred LHSV is in the range of 0.2 to 10/hr, and a preferred hydrogen/raw material proportion is in the range of 0.2 to 10 mol/mol.

Treatment in Oxidizing Atmosphere

The catalytic activity of the catalyst of the present invention can be increased by the heat treatment of it in an oxidizing atmosphere before or after use. Usually, the heat treatment is carried out at 300 to 500° C. in an atmosphere in which oxygen exists, such as air. The content of oxygen in the atmosphere is preferably 0.1 to 50% by volume, particularly 1 to 30% by weight. Mixtures of nitrogen and oxygen and of nitrogen and air, air, etc. can be used advantageously. In particular, a treating temperature of 350 to 480° C. and a treating time of 0.1 to 100 hours are preferred. The treating pressure may be a reduced pressure, atmospheric pressure, and super-atmospheric pressure. Treatment at atmospheric pressure is convenient and preferable. Since the treatment in an oxidizing atmosphere is considered to dry the catalyst and oxidize and remove the material adsorbed thereon and the deposits attached thereto to thereby activate the catalyst, it is preferred that the air to be used contains a reduced amount of impurities such as moisture, particularly before the catalyst is used. More specifically, there can be used preferably a dehumidified atmosphere of which the relative humidity at 20° C. has been decreased to not higher than 5° C. If the treating temperature is too high, the properties of the catalyst change while too low a treating temperature results in an insufficiently dried catalyst. In either case, the activity of the catalyst decreases. This treatment is effective for a catalyst which has been left to stand in the air for a period of not shorter than 1 day, particularly not shorter than 10 days after heat treatment such as calcination in the course of the preparation of the catalyst or the catalyst used in acid-catalyzed reactions. When the treatment is carried out in a non-oxidizing atmosphere (in an air stream containing no oxygen), also, the activity of the catalyst decreases.

After treatment in an oxidizing atmosphere, the adsorption of moisture to the catalyst must be avoided. For this purpose, it is preferred that the treatment is conducted after the catalyst is introduced into a reaction apparatus or reactor and start the target acid-catalyzed reaction without introduction of the air substantially. When the target acid-catalyzed reaction is carried out in a reducing atmosphere such as a hydrogen atmosphere, it is preferred that the reaction not be started before the atmosphere can be replaced by an inactive atmosphere such as an inert gas, e.g., nitrogen gas or rare gas such as argon. It should be noted that since its activity will not decrease greatly when the catalyst is exposed to the air for a period of about 1 day, in the case of a small scale reaction apparatus, the treatment in an oxidizing atmosphere may be carried out outside the reaction vessel, and then catalyst is introduced into the reaction vessel.

The treatment in the above-mentioned oxidizing atmosphere can be applied to the regeneration of a catalyst which has been used in a reaction apparatus or a reactor and whose activity has decreased. In particular, when a carbonaceous substance, such as "coke", is deposited on the catalyst, it is preferred that the concentration of oxygen is adjusted to 0.1 to 20% by volume, particularly 0.2 to 5% by volume so that the carbonaceous substance is not oxidized abruptly.

EXAMPLES

Hereinafter, the invention will be explained in more detail by examples.

In the examples, measurement methods and the like are as described below.

Method for Measuring Average Particle Diameter of Agglomerated Particles

Measurement was made by a wet measuring method using a MICROTRAC particle size analyzer manufactured by Nikkiso Co., Ltd. In this method, powder is dispersed in water, a laser beam is irradiated onto a group of agglomerated particles that flow, and particle size analysis is performed based on forward scattering light.

Method for Measuring Aspect Ratio

Powder was observed on a transmission electron microscope H-9000UHR manufactured by Hitachi Ltd. and 10 particles were extracted at random from the particles present in the image field, ratios of the major axis and minor axis of the respective particles were determined, and an average value was calculated therefrom.

Method for Measuring Pore Distribution

The range of a pore diameter of 0.05 to 10 μm was measured by a mercury injection method using an AutoPore 9200 type analyzer manufactured by Micromeritics Co. The range of a pore diameter of 0.05 μm or less was measured by a nitrogen adsorption method using an ASAP2400 type analyzer manufactured by Micromeritics Co.

Water Stability Test 50 cylindrical pellets of 1.5 mm in diameter and 5 mm in length selected at random were dipped in 10 ml of water at room temperature and left for 15 minutes, and changes in the shape of pellets were examined. That the shape was maintained means that all 50 pellets kept their shape before the dipping in water, without powdering or cracking.

Method for Measuring Average Crushing Strength

Side surface crushing strength of a sample that is cylindrically extrusion molded, dried and calcined was measured using a TH-203CP tablet crushing strength measuring apparatus manufactured by Toyama Sangyo Co., Ltd. The measurement probe used had a tip of a cylindrical shape having a diameter of 4.5 mm. The operation of applying a sample to be measured to the center of a side surface of the cylindrical surface and conducting measurement was repeated 20 times and an average value was calculated therefrom.

Method for Calculating S28.2/S30.2 Ratio

Peaks of tetragonal crystal and of monoclinic crystals of zirconia were separated from an X-ray diffraction chart, and a ratio of the peak area of monoclinic zirconia at 2θ=28.2° to the peak area of tetragonal zirconia at 2θ=30.2° was calculated. When the S28.2/S30.2 ratio was not more than 0.02, the monoclinic crystal peak was unclear and undetectable. The X-ray diffraction chart was measured under the following conditions.

Wide angle X-ray measuring apparatus; RAD-1C manufactured by Rigaku Denki Co., Ltd. Horizontal goniometer X-ray bulb; Enclosed tube type Cu bulb (Output power 30 kV-20 mA, wavelength 1.5406 Å)

Measurement region (2θ); 3–90°

Step width; 0.02°

Scan speed; 4°/min

Slit width;
 Divergent slit (DS)=1°
 Scattering slit (SS)=1°
 Receiving slit (RS)=0.33 mm Smoothing condition; Savitzky, Golay's 15 point weighted smoothing method Peak separation applied region (2θ); 26.5 to 32.5° Separation target peak number; 4 (monoclinic crystal 2, tetragonal crystal 1, amorphous 1) Crystal species ratio calculation applied peak;

Monoclinic; 2θ=28.2° (d=3.163, hkl=111) Tetragonal; 2θ=30.2° (d=2.960, hkl=111)

Catalyst A

Of commercially available dry hydrated zirconia preparations, there was used a powder having an average particle diameter of 1.2 µm as the zirconia powder. Also, of commercially available hydrated alumina (pseudoboehmite) powders, there was used an alumina powder having a fibrous particle form. The alumina powder had an aspect ratio of 58 and an average particle diameter of 10 µm. There were added 1200 g of the zirconia powder, 800 g of alumina powder and further 383 g of ammonium sulfate and these were kneaded for 45 minutes in a kneader with stirring vanes while adding water. The resultant kneaded product was extruded through an extruder having a circular opening of 1.6 mm in diameter to shape into cylindrical pellets, which were dried at 110° C. to obtain dry pellets. The dry pellets were tested for water stability. As a result, all the pellets did not crack or powder and maintained their shape as they are. Subsequently, the dry pellets were calcined at 650° C. for 2 hours to obtain catalyst A.

Measurement of the pore distribution of catalyst A for pores with a pore diameter of 0.05 to 10 µm revealed a pore distribution which has a clear peak at a pore diameter of 0.18 µm but no other clear peak. The pores having a pore diameter of not less than 0.05 µm and not more than 1 µm occupied 0.18 ml/g and pores having a pore diameter of above 1 µm and not more than 10 µm occupied 0.01 ml/g or less. Also, measurement of the pore distribution of pores having a pore diameter of not more than 500 Å indicated an average pore diameter of 50 Å.

Shaped catalyst A was in the form of a cylinder having an average diameter of 1.5 mm and an average length of 5 mm and a water stability test thereof revealed that all the pellets maintained their shape as they did not crack or powder. Also, its average crushing strength was revealed to be 4.5 kg. The S28.2/S30.2 ratio of catalyst A was 0.04 and substantially no monoclinic structure existed.

Catalyst B

Of commercially available dry hydrated zirconia preparations, there was used a powder having an average particle diameter of 15 µm as the zirconia powder. Also, of commercially available hydrated alumina (pseudoboehmite) powders, there was used an alumina powder having a plate-like particle form. The alumina powder had an aspect ratio of 2, an average particle diameter of 20 µm. Catalyst B was obtained by fabricating in the same manner as catalyst A except for using these zirconia powder and the alumina powder. The dry pellets under fabrication were tested for water stability, which revealed that all the pellets were powdered.

Measurement of the pore distribution of catalyst B for pores with a pore diameter of 0.05 to 10 µm revealed a pore distribution which has a clear peak at a pore diameter of 1.7 µm but no other clear peak. The pores having a pore diameter of not less than 0.05 µm and not more than 1 µm occupied 0.07 ml/g and pores having a pore diameter of above 1 µm and not more than 10 µm occupied 0.12 ml/g. Also, measurement of the pore distribution of pores having a pore diameter of not more than 500 Å indicated an average pore diameter of 45 Å.

Shaped catalyst B had a cylindrical shape having an average diameter of 1.5 mm and an average length of 5 mm and a water stability test thereof revealed that 10 out of 50 pellets were cracked or powdered. Also, its average crushing strength was revealed to be 2.8 kg. The S28.2/S30.2 ratio of catalyst B was 0.04 and substantially no monoclinic structure existed.

Catalyst C

To 50 g of catalyst A was spray-supported an aqueous solution of chloroplatinic acid such that the amount of platinum in the catalyst was 0.5%. After it was dried, the catalyst was calcined at 550° C. for 2 hours to obtain catalyst C. The pore distribution and crystal structure of catalyst C were substantially the same as those of catalyst A. A water stability test on catalyst C revealed that all the pellets maintained their shape as they were without cracking or powdering. An average crushing strength was 4.0 kg.

Catalyst D

To 50 g of catalyst B was spray-supported an aqueous solution of chloroplatinic acid such that the amount of platinum in the catalyst was 0.5%. After it was dried, the catalyst was calcined at 550° C. for 2 hours to obtain catalyst D. The pore distribution and crystal structure of catalyst D were substantially the same as those of catalyst B. A water stability test on catalyst D revealed that 8 out of 50 pellets were cracked or powdered. An average crushing strength was 2.5 kg.

Catalysts E and F

A dry hydrated zirconia powder having an average particle diameter of 1.2 µm obtained by drying commercially available zirconium hydroxide was used as the zirconia powder. Also, of the commercially available hydrated alumina (pseudoboehmite) powders, an alumina powder having a fibrous particle form was used. The alumina powder had an aspect ratio of 58 and an average particle diameter of 10 µm. There were added 1500 g of the zirconia powder, 500 g of the alumina powder and further 383 g of ammonium sulfate and these were kneaded for 45 minutes in a kneader with stirring vanes while adding water. The resultant kneaded product was extruded through an extruder having a circular opening of 1.6 mm in diameter and dried at 110° C. to obtain dry pellets. The dry pellets were tested for water stability. As a result, all the pellets did not crack or powder and maintained their shape as they are. Subsequently, the dry pellets were calcined at 650° C. for 2 hours to obtain catalyst E, which was a catalyst of a zirconia shaped material having a sulfureous component thereon.

Measurement of the pore distribution of catalyst E for pores with a pore diameter of 0.05 to 10 µm revealed a pore distribution which has a clear peak at a pore diameter of 0.22 µm but no other clear peak. The pores having a pore diameter of not less than 0.05 µm and not more than 1 µm occupied 0.18 ml/g and pores having a pore diameter of above 1 µm and not more than 10 µm occupied 0.01 ml/g. Also, measurement of the pore distribution of pores having a pore diameter of not more than 500 Å indicated an average pore diameter of 48 Å.

Shaped catalyst E had a cylindrical shape having an average diameter of 1.5 mm and an average length of 5 mm and a water stability test thereof revealed that all the pellets maintained their shape as they were without cracking or powdering. Also, its average crushing strength was revealed to be 3.5 kg. The S28.2/S30.2 ratio of catalyst E was 0.05 and substantially no monoclinic structure existed.

To 50 g of catalyst E was added 125 ml of an aqueous solution of chloroplatinic acid such that the amount of platinum in the catalyst was 0.5%. After it was dried, the catalyst was calcined at 550° C. for 2 hours to obtain catalyst F, which was a catalyst composed of a platinum-containing sulfated zirconia/alumina shaped material. The pore distribution and crystal structure of catalyst F were substantially the same as those of catalyst E. A water stability test on catalyst F revealed that all the pellets maintained their shape as they were without cracking or powdering. An average crushing strength was 3.3 kg.

Catalyst G

Of commercially available dry hydrated zirconia preparations, there was used a powder having an average particle diameter of 1.2 μm as the zirconia powder. Also, of commercially available hydrated alumina (pseudoboehmite) powders, there was used an alumina powder having a fibrous particle form. The alumina powder had an aspect ratio of 58 and an average particle diameter of 10 μm. There were added 300 g of the zirconia powder and 300 g of alumina powder and these were kneaded for 2 hours in a kneader with stirring vanes while adding water. The resultant kneaded product was extruded through an extruder having a circular opening of 1.6 mm in diameter to shape into cylindrical pellets, which were dried at 110° C. to obtain dry pellets. Subsequently, the dry pellets were calcined at 650° C. for 2 hours to obtain support G.

Measurement of the pore distribution of support G for pores with a pore diameter of 0.05 to 10 μm revealed a pore distribution which had a clear peak at a pore diameter of 0.25 μm but no other clear peak. The pores having a pore diameter of not less than 0.05 μm and not more than 1 μm occupied 0.20 ml/g and pores having a pore diameter of above 1 μm and not more than 10 μm occupied not more than 0.01 ml/g. Also, measurement of the pore distribution of pores having a pore diameter of not more than 500 Å indicated an average pore diameter of 65 Å.

Shaped support G was in a cylindrical shape having an average diameter of 1.5 mm and an average length of 5 mm and a water stability test thereof revealed that all the pellets maintained their shape as they did not crack or powder. Also, its average crushing strength was revealed to be 4.8 kg. The S28.2/S30.2 ratio of support G was not more than 0.02 and substantially no monoclinic structure existed.

To support G was added 125 ml of an aqueous solution of chloroplatinic acid such that the amount of platinum in the catalyst was 0.5%. After it was dried, 125 ml of an aqueous solution of 0.5 mol/l sulfuric acid was added and it was dried again, followed by calcination of the catalyst at 600° C. for 2 hours to obtain catalyst G. Shaped catalyst G was in a cylindrical shape having an average diameter of 1.5 mm and an average length of 5 mm. The S28.2/S30.2 ratio of catalyst G was not more than 0.02 and substantially no monoclinic structure existed.

Measurement of the pore distribution of catalyst G for pores with a pore diameter of 0.05 to 10 μm revealed a pore distribution which had a clear peak at a pore diameter of 0.22 μm but no other clear peak. The pores having a pore diameter of not less than 0.05 μm and not more than 1 μm occupied 0.18 ml/g and pores having a pore diameter of above 1 μm and not more than 10 μm occupied not more than 0.01 ml/g. Also, measurement of the pore distribution of pores having a pore diameter of not more than 500 Å indicated an average pore diameter of 60 Å.

Shaped catalyst G was in the form of a cylinder having an average diameter of 1.5 mm and an average length of 5 mm and a water stability test thereof revealed that all the pellets maintained their shape as they did not crack or powder. Also, its average crushing strength was revealed to be 4.6 kg. The S28.2/S30.2 ratio of support G was not more than 0.02 and substantially no monoclinic structure existed.

Deteriorated Catalyst H 40 g of catalyst G was treated at 450° C. for 24 hours in a hydrogen stream of 10 kg/cm$^2$-G, 600 ml/minute to obtain deteriorated catalyst H. The pore distribution and crystal structure of deteriorated catalyst H were substantially the same as those of catalyst G. A water stability test on deteriorated catalyst H revealed that all the pellets maintained their shape as they did not crack or powder.

Treated Catalyst I 10 g of deteriorated catalyst H was calcined at 550° C. for 2 hours in air to obtain treated catalyst I. The pore distribution and crystal structure of treated catalyst I were substantially the same as those of catalyst G. A water stability test on treated catalyst I revealed that all the pellets maintained their shape as they did not crack or powder.

Treated Catalyst J

To 10 g of deteriorated catalyst H was added 150 ml of an aqueous solution of 0.5 mol/l sulfuric acid for contact and then excess aqueous sulfuric acid solution was removed by filtration, dried and calcined at 550° C. for 2 hours to obtain treated catalyst J. The pore distribution and crystal structure of catalyst J were substantially the same as those of catalyst G. A water stability test on treated catalyst J revealed that all the pellets maintained their shape as they did not crack or powder.

Treated Catalyst K

To 10 g of deteriorated catalyst H was added 150 ml of an aqueous solution of 0.5 mol/l ammonium sulfate for contact and then excess aqueous ammonium sulfate solution was removed by filtration, dried and calcined at 550° C. for 2 hours to obtain treated catalyst K. The pore distribution and crystal structure of treated catalyst K were substantially the same as those of catalyst G. A water stability test on treated catalyst K revealed that all the pellets maintained their shape as they did not crack or powder.

Acylation Reaction 20.0 g of catalyst pulverized in a mortar and sieved through not more than 32 mesh in order to increase the efficiency of stirring was charged in an autoclave and pretreated at 400° C. for 1 hour in an atmosphere of air. Thereinafter, the inside of the autoclave was rendered a nitrogen atmosphere without introducing the open air, and 225 g of chlorobenzene and 35 g of p-chlorobenzoyl chloride were added, followed by reaction at 135° C. with stirring. After 3 hours' reaction, the reaction mixture was analyzed by gas chromatography.

The yield of dichlorobenzophenone, acylated form, was 27% when catalyst A was used, 24% when catalyst B was used, and 29% when catalyst E was used. For comparison, an acylation reaction was carried out in the same manner as above except that catalyst E was used and the atmosphere of pretreatment was nitrogen, with the result that the yield of dichlorobenzophenone was 26%. n-Hexane Isomerization Reaction 1.

4 cc of each of catalysts (catalysts C and D) granulated to 16 to 24 mesh was filled in a fixed bed flow type reactor of 50 cm in length and 1 cm in inner diameter and pretreated, followed by an isomerization reaction of n-hexane. The pretreatment was carried out under the conditions of a temperature: 40° C., pressure: atmospheric pressure, atmosphere: air, for 1 hour. Thereinafter, the inside of the reactor was rendered a nitrogen atmosphere without introducing air and then a hydrogen atmosphere before the isomerization reaction could be started.

The isomerization reaction of n-hexane was carried out under the conditions of a reaction temperature: 200° C., reaction pressure (gauge pressure): 10 kgf/cm$^2$, LHSV=1.5/hr and hydrogen/oil ratio (H$_2$/oil) : 5 (mol/mol).

Conversion rate and selectivity which indicate the activity of a catalyst were calculated and evaluated by the following using a conversion rate into n-hexane and a value of 2,2'-dimethylbutane/noncyclic C6.

Conversion rate into n-Hexane=[1−(% by weight of n-hexane in produced oil/% by weight of n-hexane in raw material oil)]× 100 (%)

2,2'-Dimethylbutane/noncyclic C6=(% by weight of 2,2'-dimethylbutane in produced oil/% by weight of whole noncyclic hydrocarbon having 6 carbon atoms in produced oil)×100 (%)

The composition at the reaction pipe outlet after 20 hours from the start of the oil flow was analyzed by gas chromatography, with the result that the conversion rate of n-hexane was 88.6% in the case of catalyst C and 86.3% in the case of catalyst D and the value of 2,2'-diemthylbutane/noncyclic C6 was 26.2% in the case of catalyst C and 20.5% in the case of catalyst D.

n-Hexane Isomerization reaction 2

Using catalyst F, there was carried out a n-hexane conversion reaction similar to the above-mentioned isomerization reaction 1 under the conditions of a reaction temperature: 180° C., a reaction pressure (gauge pressure): 10 kgf/cm$^2$, LHSV=1.5/hr, a hydrogen/oil ratio (H$_2$/oil): 5 (mol/mol) with varied pretreatment conditions. The composition at the reaction pipe outlet after 20 hours from the start of oil flow was analyzed by gas chromatography for reactions in which temperature, atmosphere and pressure of the pretreatment conditions were varied. The results obtained are shown in Table 1.

TABLE 1

| Temperature (° C.) | Atmosphere | Pressure | Conversion into n-hexane (%) | 2,2' Dimethylbutane/noncyclic C6 (%) |
|---|---|---|---|---|
| 400 | Air | Atmospheric pressure | 86.4 | 21.0 |
| 500 | Air | Atmospheric pressure | 86.1 | 20.2 |
| 300 | Air | Atmospheric pressure | 86.0 | 20.1 |
| 300 | Air | 10 | 86.2 | 20.5 |
| 600 | Air | Atmospheric pressure | 84.5 | 15.2 |
| 200 | Air | Atmospheric pressure | 85.0 | 17.5 |
| 400 | Nitrogen | Atmospheric pressure | 85.3 | 18.5 |
| 400 | Hydrogen | Atmospheric pressure | 20.0 | 0.5 |
| 300 | Hydrogen | 10 | 84.8 | 16.2 | n-Hexane Isomerization Reaction 3 n-Hexane Isomerization Reaction 3

Activation treatment of a catalyst which has been deactivated after the reaction was carried out. Catalyst F was used in the above-mentioned isomerization reaction 2 for 100 hours to deteriorate the catalyst, using nitrogen instead of hydrogen. The catalyst was pretreated in a different atmosphere and the change in activity was measured. A hydrogen atmosphere, nitrogen atmosphere, and nitrogen containing 2% by volume of oxygen were used as the atmosphere and pretreatment was carried out at 400° C. for 2 hours. The activity was evaluated by carrying out the same reaction as the above-mentioned isomerization reaction 2 and analyzing the composition at the reaction pipe outlet after 20 hours from the start of oil flow by gas chromatography. Table 2 the results.

TABLE 2

| Temperature (° C.) | Atmosphere | Conversion of n-hexane (%) | 2,2'-dimethylbutane/noncyclic C6 (%) |
|---|---|---|---|
| | Deactivation | <0.1 | <0.1 |
| 400 | 2% oxygen + nitrogen | 86.2 | 20.6 |
| 400 | 100% nitrogen | <0.1 | <0.1 |
| 400 | 100% hydrogen | <0.1 | <0.1 | n-Heptane Conversion Reaction

One (1) g of catalyst shaped into grains of 16 to 24 mesh was filled in a fixed bed flow type reactor of 50 cm in length and 1 cm in inner diameter and the reaction was carried out under the conditions of a reaction temperature: 200° C., a reaction pressure: 4 kg/cm$^2$-G, WHSV: 3.4/h, and a hydrogen/raw material ratio (H$_2$/oil) : 5 mol/mol. As the pretreatment of the catalyst, reduction with hydrogen at 300° C. for 1 hour was carried out before the conversion reaction. Conversion rate, which indicates the activity of the catalyst, was calculated using the conversion rate into n-heptane as below and evaluated.

Conversion rate into n-heptane=[1−(% by weight of n-heptane in produced oil/% by weight of n-heptane in raw material oil)]× 100 (%)

Analyzing the conversion rate into n-heptane after 2 hours from the start of the reaction by gas chromatography, n-heptane conversion activity was evaluated. Table 3 shows the results.

TABLE 3

| Catalyst | Conversion into n-heptane |
|---|---|
| G | 67% |
| H | 3% |
| I | 10% |
| J | 67% |
| K | 66% |

INDUSTRIAL APPLICABILITY

The present invention relates to a shaped solid acid catalyst comprising a support having a specified pore structure, and the catalyst can have sufficient mechanical strength and at the same time exhibit excellent catalytic activity because of the presence of the specified pore structure in the shaped catalyst. Since it is a shaped material, the catalyst can be easily separated from the reactants, which allows reuse of the catalyst as well as facilitates the reclamation of a used catalyst.

The solid acid catalyst of the present invention is useful in a variety of acid-catalyzed reactions such as isomerization, disproportionation, alkylation, esterification, acylation, etherification, and polymerization.

What is claimed is:

1. A method for producing a solid acid catalyst comprises the steps of:
   fabricating a support comprising a portion of zirconia and/or hydrated zirconia and a portion of alumina and/or hydrated alumina and having a peak in diameter in the range of 0.05 to 1 µm in a pore diameter distribution of 0.05 to 10 µm; and
   having a sulfureous component supported on the support.

2. The method for producing a solid acid catalyst as claimed in claim 1, wherein pores having a pore diameter of not less than 0.05 μm and not more than 1 μm occupy a pore volume of 0.05 to 0.5 ml/g and pores having a pore diameter of above 1 μm and not more than 10 μm occupy a pore volume of below 0.05 ml/g.

3. The method for producing a solid acid catalyst as claimed in claim 1, wherein said step for fabricating a support is a step including kneading powder comprising zirconium hydroxide and/or hydrated oxide whose agglomerated particles having an average particle diameter of 0.2 to 10 μm with powder comprising aluminum hydroxide and/or hydrated oxide having a fibrous particle form, and shaping the mixture.

4. The method for producing a solid acid catalyst as claimed in claim 1, wherein said step for fabricating a support and said step for having a sulfureous component supported on the support are performed in one step.

5. The method for producing a solid acid catalyst as claimed in claim 1, wherein said step for having a sulfureous component supported on the support comprises after fabricating a support contacting a sulfureous compound with the support and calcining the support at a temperature higher than 300° C. and lower than 800° C.

6. A method for producing a solid acid catalyst comprising the step of having a sulfureous component supported, the step including:

contacting a solid acid catalyst, which has been produced by the production method as claimed in claim 1 and used until its activity has been decreased, as a support with a sulfureous compound; and calcining the support at a temperature higher than 300° C. and lower than 800° C.

7. The method for producing a solid acid catalyst as claimed in claim 1, wherein said solid acid catalyst comprises at least one metal selected from the group consisting of Group 8 metals, Group 9 metals and Group 10 metals.

8. A method for producing a solid acid catalyst comprising the step of treating a solid acid catalyst, which has been produced by the production method as claimed in claim 1 and used until its activity is decreased, in an oxidizing atmosphere at a temperature of 300 to 500° C.

9. A solid acid catalyst used in an acid-catalyzed reaction, comprising a support comprising a portion of zirconia and/or hydrated zirconia, a portion of alumina and/or hydrated alumina, and a sulfureous component and having a peak in diameter in the range of 0.05 to 1 μm in a pore diameter distribution of 0.05 to 10 μm.

10. The solid acid catalyst as claimed in claim 9, wherein pores having a pore diameter of not less than 0.05 μm and not more than 1 μm occupy a pore volume of 0.05 to 0.5 ml/g and pores having a pore diameter of above 1 μm and not more than 10 μm occupy a pore volume of below 0.05 ml/g.

11. The solid acid catalyst as claimed in claim 9, wherein said acid-catalyzed reaction is a conversion reaction of hydrocarbons.

12. The solid acid catalyst as claimed in claim 9, wherein said solid acid catalyst comprises at least one metal selected from the group consisting of Group 8 metals, Group 9 metals and Group 10 metals.

13. An acid-catalyzed reaction method comprising the steps of carrying out an acid-catalyzed reaction selected from the group consisting of an isomerization reaction, a disproportionation reaction, a nitration reaction, a decomposition reaction, an alkylation reaction, an esterification reaction, an acylation reaction, an etherification reaction and a polymerization reaction using a solid acid catalyst as claimed in claim 9 until its activity has decreased, treating the solid acid catalyst in an oxidizing atmosphere at a temperature of 300 to 500° C. to regenerate the catalyst, and then carrying out said acid-catalyzed reaction using the regenerated catalyst.

14. An acid-catalyzed reaction method for carrying out an acid-catalyzed reaction selected from the group consisting of an isomerization reaction, a disproportionation reaction, a nitration reaction, a decomposition reaction, an alkylation reaction, an esterification reaction, an acylation reaction, an etherification reaction and a polymerization reaction of a hydrocarbon, or a derivative thereof, with a solid acid catalyst as claimed in claim 9, comprising the steps of: introducing the solid acid catalyst into a reaction vessel; treating the solid acid catalyst in an oxidizing atmosphere at a temperature of 300 to 500° C.; and carrying out the acid-catalyzed reaction using the treated catalyst.

15. A method for isomerizing a hydrocarbon, or a derivative thereof, comprising the steps of: introducing a solid acid catalyst as claimed in claim 9 into a reaction vessel; treating said catalyst at a temperature of 300 to 500° C. in an oxidizing atmosphere; replacing the oxidizing atmosphere with an inert atmosphere; and bringing the catalyst into contact with the hydrocarbon, or a derivative thereof, in a hydrogen atmosphere to isomerize the hydrocarbon, or a derivative thereof.

* * * * *